(12) United States Patent
Siegert et al.

(10) Patent No.: US 7,754,900 B2
(45) Date of Patent: Jul. 13, 2010

(54) METHOD FOR THE PRODUCTION OF DIOXOLANE

(75) Inventors: Markus Siegert, Heidelberg (DE); Neven Lang, Mannheim (DE); Eckhard Stroefer, Mannheim (DE); Achim Stammer, Freinsheim (DE)

(73) Assignee: BASF SE, Ludwigshafen (DE)

( * ) Notice: Subject to any disclaimer, the term of this patent is extended or adjusted under 35 U.S.C. 154(b) by 44 days.

(21) Appl. No.: 12/066,093

(22) PCT Filed: Sep. 6, 2006

(86) PCT No.: PCT/EP2006/066086

§ 371 (c)(1),
(2), (4) Date: Mar. 7, 2008

(87) PCT Pub. No.: WO2007/028809

PCT Pub. Date: Mar. 15, 2007

(65) Prior Publication Data

US 2008/0255376 A1  Oct. 16, 2008

(30) Foreign Application Priority Data

Sep. 7, 2005 (DE) ........................ 10 2005 042 505

(51) Int. Cl.
*C07D 317/12* (2006.01)

(52) U.S. Cl. ........................................ 549/430; 203/38

(58) Field of Classification Search ................. 549/430; 203/38

See application file for complete search history.

(56) References Cited

U.S. PATENT DOCUMENTS 6,713,640 B2 * 3/2004 Miller et al. ................. 549/430

FOREIGN PATENT DOCUMENTS

DE  1279025       10/1968
JP  5-271217 A    10/1993

OTHER PUBLICATIONS

Chopade et al., Reactive and Functional Polymers, 34, 37-45, 1997.*

* cited by examiner

*Primary Examiner*—Janet L Andres
*Assistant Examiner*—David E Gallis

(57) ABSTRACT

Processes comprising: providing a reactive distillation column having an upper region, a middle region and a lower region; feeding ethylene glycol and an aqueous formaldehyde solution into the reactive distillation column in the middle region of the reactive distillation column; reacting the ethylene glycol and the aqueous formaldehyde solution in the reactive distillation column in the presence of a catalyst to form dioxolane; removing a product stream comprising dioxolane in an amount of at least 75% by weight from the upper region of the reactive distillation column; and removing a bottom stream comprising one or more components having boiling points higher than dioxolane from the lower region of the reactive distillation column.

Figure 1:
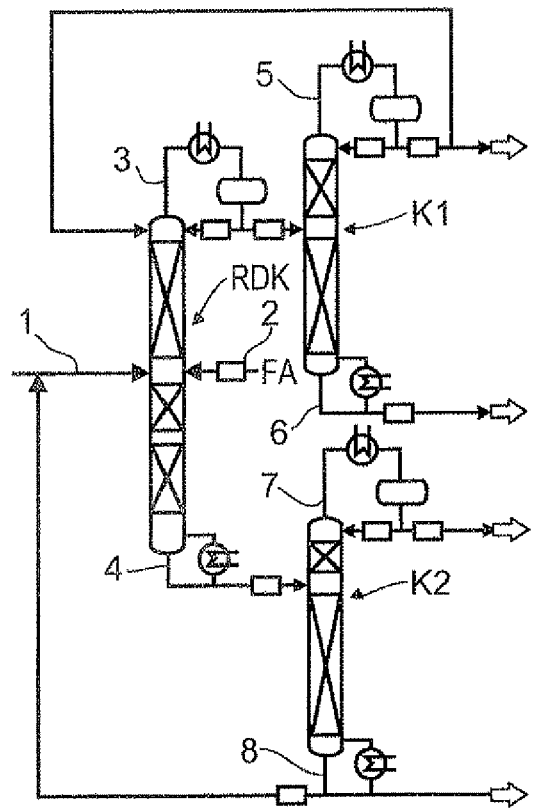

17 Claims, 3 Drawing Sheets

METHOD FOR THE PRODUCTION OF DIOXOLANE

CROSS-REFERENCE TO RELATED APPLICATIONS

This application is a national stage application, under 35 U.S.C. §371, of PCT/EP2006/066086, filed Aug. 23, 2006, which claims priority of German Patent Application No. 10 2005 042 505.4, filed Sep. 7, 2005.

BACKGROUND OF THE INVENTION 1,3-Dioxacyclopentane, hereinafter referred as dioxolane, is a derivative of ethylene glycol which is used industrially and can be prepared by reacting ethylene glycol with an aqueous formaldehyde solution in the presence of acid catalysts such as sulfuric acid, boron trifluoride, zinc chloride or acid ion exchangers. Pure dioxolane can be isolated from the reaction mixture using various separation methods, in particular by distillation or extraction.

Dioxolane is used, in particular, as comonomer in the polymerization of trioxane to form polyoxymethylene copolymers.

The by far most frequently used method of separating liquid mixtures into fractions or pure components is distillation or rectification. The separating action of this powerful process is based on mass transfer between a gaseous phase and a liquid phase which are conveyed in direct contact in countercurrent to one another.

DE A 1 279 025 discloses a process for the continuous purification of a dioxolane-comprising reaction mixture from the reaction of ethylene glycol with formaldehyde in the presence of acid catalysts, in which a crude dioxolane which still comprises relatively large amounts of water, unreacted formaldehyde and relatively small amounts of acid and alcohol, e.g. formic acid and methanol, is firstly obtained by distillation and is fed in gaseous form into a distillation column in which an azeotropic mixture of dioxolane and water comprising not more than 10% by weight, generally about 7% by weight, of water is distilled off at the top. The azeotropic mixture is cooled to about 20-40° C. and is treated in countercurrent with alkali metal hydroxide and/or a concentrated aqueous alkali metal hydroxide solution, by means of which it is largely freed of water and other impurities. After the alkali treatment, it is fractionally distilled to give purified dioxolane having an extremely low water content of 50 ppm or less via the bottom of the column. The process has the disadvantage that a plurality of distillation columns are necessary to obtain pure dioxolane, resulting in corresponding capital, operating and in particular energy costs.

BRIEF SUMMARY OF THE INVENTION

The present invention relates to processes for preparing dioxolane.

It was therefore an object of the invention to provide a simpler, in particular more economical, process for preparing pure dioxolane which can, in particular, be carried out in a smaller number of apparatuses with correspondingly lower capital costs.

The invention provides a process for preparing dioxolane by reacting ethylene glycol with formaldehyde in aqueous solution in the presence of catalysts, wherein the reaction is carried out in a reactive distillation column, with the starting materials ethylene glycol and aqueous formaldehyde solution being fed into the reactive distillation column in the middle region of the column and a dioxolane-comprising stream comprising at least 75% by weight of dioxolane being taken off from the upper region of the reactive distillation column and a bottom stream comprising components having boiling points higher than that of dioxolane being taken off.

It has been found that it is possible to carry out the reaction of ethylene glycol and aqueous formaldehyde solution in a reactive distillation column and to obtain a stream having a high proportion of dioxolane of at least 75% by weight of dioxolane from the upper region of the reactive distillation column.

DETAILED DESCRIPTION OF THE INVENTION

Reactive distillations are known and are, as is known, processes in which a reaction and a separation by distillation take place. Such processes are carried out in reactive distillation columns which are equipped with separation-active internals or into which a catalyst is applied or introduced. These can be trays on which a catalyst bed is installed, but are in particular packings in which the catalyst is introduced into the packing or the packing is coated with catalyst.

In the present process, the starting materials ethylene glycol and formaldehyde in aqueous solution are fed, in particular separately from one another, into the middle region of a reactive distillation column which is provided with reactive internals. In one embodiment, the two feed streams are fed to the reactive distillation column at the same height.

Suitable catalysts are in principle all known catalysts for the reaction of glycol with aqueous formaldehyde solution. These are acid catalysts such as sulfuric acid, boron trifluoride, zinc chloride or acid ion exchangers.

The reactive distillation column can be operated at a pressure at the top in the range from 0.01 to 5 bar absolute, preferably from 0.15 to 2.50 bar absolute, particularly preferably from 0.20 to 1.50 bar absolute. It preferably has from 2 to 75, in particular from 5 to 50 and particularly preferably from 10 to 30, theoretical plates.

A stream having a high dioxolane content of at least 75% by weight, preferably at least 80% by weight, particularly preferably at least 85% by weight, is taken off from the upper region of the reactive distillation column. The process can, in particular, be carried out so that a mixture having a composition close to the binary azeotrope of dioxolane/water is obtained from the upper region of the reactive distillation column under the conditions of the pressure at the top of the reactive distillation column and the corresponding temperature.

In this variant, the mixture having the composition close to the composition of the binary azeotrope of dioxolane/water is worked up to obtain dioxolane in a subsequent pressure swing rectification: for this purpose, the azeotrope of dioxolane/water is fed into the middle region of a first distillation column which is operated at a pressure at the top which is above the pressure at the top of the reactive distillation column, in particular at least 0.1 bar higher than the pressure at the top of the reactive distillation column.

An overhead stream comprising the binary azeotrope of dioxolane/water is taken off from the first distillation column under the conditions of temperature and pressure at the top of the first distillation column and a stream comprising pure dioxolane is taken off from the stripping section of the first distillation column, in particular from the bottom of the first distillation column.

For the present purposes, pure dioxolane is a stream which comprises at least 90% by weight, in particular at least 95% by weight or else at least 99% by weight, of dioxolane.

The overhead stream from the first distillation column, which comprises the binary azeotrope of dioxolane/water under the conditions of temperature and pressure at the top of the first distillation column, is recycled to the reactive distillation column, preferably in the upper part of this.

The bottom stream from the reactive distillation column, which comprises components having boiling points higher than that of dioxolane, in particular ethylene glycol and water, is preferably fed to a second distillation column which is, in particular, operated at a pressure at the top in the range from 0.01 to 5.00 bar absolute, more preferably from 0.15 to 2.5 bar absolute or else from 0.20 to 1.50 bar absolute, and from which a water-rich overhead stream having a water content of greater than 75% by weight, preferably greater than 90% by weight, particularly preferably greater than 99% by weight, is taken off and a bottom stream which is rich in ethylene glycol and comprises at least 90% by weight of ethylene glycol is taken off.

To avoid accumulation of high boilers in the plant, preference is given to discharging a small substream of the bottom stream. The remainder of the bottom stream is recycled to the reactive distillation column. It is preferably mixed with the ethylene glycol stream and fed into the reactive distillation column.

In a particularly advantageous variant of the process, the reactive distillation column is configured as a dividing wall column. Dividing wall columns are, as is known, columns in which transverse mixing of liquid and vapor streams in the subregions of the column is prevented by installation of a dividing wall.

The dividing wall column has a dividing wall which is aligned in the longitudinal direction of the column and divides the interior of the column into a feed region, an offtake region, a lower combined column region and an upper combined column region.

Separation-active internals, in particular packings or trays, and the catalyst for the reaction to form dioxolane, which may be installed on or in the internals, are installed in the dividing wall column.

The starting materials ethylene glycol and aqueous formaldehyde solution are fed into the dividing wall column in the feed region thereof, e.g. at the same height. In one process variant, ethylene glycol is introduced above the aqueous formaldehyde solution into the feed region of the dividing wall column.

A dioxolane-comprising stream having a minimum dioxolane content of 75% by weight is taken off from the upper region, in particular from the top, of the dividing wall column.

A stream comprising components having boiling points higher than that of dioxolane, in particular ethylene glycol, is taken off from the bottom of the column.

A water-rich stream having a water content of greater than 75% by weight, preferably greater than 90% by weight, particularly preferably greater than 99% by weight, is taken off from the offtake region of the dividing wall column and is fed to the wastewater requiring treatment.

In one process variant, an overhead stream having the composition of the binary azeotrope of dioxolane/water is taken off from the dividing wall column and is fed to a first distillation column which has a pressure at the top which is higher than the pressure at the top of the dividing wall column, in particular by 0.1 bar, and which is provided, in particular, with from 2 to 75, preferably from 5 to 50, theoretical plates.

An overhead stream comprising the binary azeotrope of dioxolane/water under the conditions of temperature and pressure at the top of the first distillation column is taken off from the first distillation column and a stream comprising pure dioxolane which corresponds to the definition given above is taken off from the bottom.

In a particularly advantageous process variant, the starting materials ethylene glycol and aqueous formaldehyde solution are fed in in a specific manner, namely the ethylene glycol is firstly fed in above the aqueous formaldehyde solution and secondly is introduced in a molar excess of ethylene glycol so that the liquid mixture in the column has an ethylene glycol content of greater than 25% by weight.

The inventors have recognized that the binary vapor/liquid phase equilibrium is altered by the presence of ethylene glycol so that the azeotrope dioxolane/water disappears completely.

If the proportion of components having boiling points lower and/or higher than that of dioxolane in the overhead stream from the reactive distillation column is still too high, it is possible to feed this stream into a first distillation column and to separate it therein into an overhead stream comprising components having boiling points lower than that of dioxolane, if appropriate a bottom stream comprising components having boiling points higher than that of dioxolane and a pure dioxolane stream from the lower region of the stripping section. If the proportion of high boilers has not exceeded the required specification, it is also possible to take off the pure dioxolane stream as bottom stream from the first distillation column.

The bottom stream from the reactive distillation column is, as in the above-described process variants, fed to a second distillation column and is separated therein into a water-rich overhead fraction and a bottom fraction which is rich in ethylene glycol and is preferably, apart from a smaller substream which is discharged, recycled to the reactive distillation column, preferably into the ethylene glycol feed stream.

In a further variant, the process can be operated without use of the first distillation column in such a way that a stream comprising components having boiling points lower than that of dioxolane are taken off at the top of the reactive distillation column and a stream comprising pure dioxolane is taken off from the upper region of the reactive distillation column, below the overhead stream.

In a particularly advantageous variant, the process can be carried out using the specific introduction of the feed streams described above, i.e. with introduction of the ethylene glycol above the aqueous formaldehyde solution and also a molar excess of ethylene glycol over formaldehyde, with the reactive distillation column being configured as a dividing wall column so that the liquid mixture in the column has an ethylene glycol content of greater than 20% by weight.

In this process variant, the ethylene glycol feed stream is introduced above the aqueous formaldehyde solution into the feed region of the dividing wall column, particularly preferably at the upper end of the column, and the aqueous formaldehyde solution is preferably fed in the middle region of the feed region of the dividing wall column.

An overhead stream comprising components having boiling points lower than that of dioxolane is taken off from the upper combined column region and pure dioxolane is taken off at a point below this, likewise from the upper combined column region.

The bottom stream comprising components having boiling points higher than that of dioxolane is preferably, apart from a small substream which is discharged, recycled to the reactive distillation column configured as a dividing wall column, in particular into the ethylene glycol feed stream.

A water-rich stream, in particular a stream having a water content of greater than 75% by weight, preferably greater than 90% by weight, particularly preferably greater than 99% by weight, is taken off from the offtake region of the dividing wall column at a theoretical plate which is, in particular, located at the same height or below the point at which the aqueous formaldehyde solution is fed in.

The invention is illustrated below with the aid of examples and a drawing.

In the drawing:

FIG. 1 schematically shows a plant for one process variant,

FIGS. 2 to 5 each schematically show plants for further preferred process variants.

Identical reference numerals in the figures denote identical or analogous features In the process scheme shown in FIG. 1, a feed stream 1 comprising ethylene glycol and a feed stream 2 comprising an aqueous formaldehyde solution are fed into a reactive distillation column RDK which has separation-active internals and, at least in subregions thereof, reactive internals. An overhead stream 3 comprising the azeotrope of dioxolane/water is taken off from the reactive distillation column, condensed in a condenser at the top of the column, part of it is returned as runback to the reactive distillation column and the remainder is fed to a first distillation column K1 which is operated at a pressure at the top which is higher than that in the reactive distillation column RDK and separated therein into an overhead stream comprising the azeotrope of dioxolane/water at the pressure at the top of the first distillation column K1, which is condensed in a condenser and part of it is recycled to the reactive distillation column RDK in the upper region thereof and the remainder is discharged. A bottom stream 6 comprising pure dioxolane is taken off from the first distillation column.

The bottom stream 4 from the reactive distillation column RDK comprises components having boiling points higher than that of dioxolane, in particular ethylene glycol and water. The bottom stream 4 from the reactive distillation column RDK is fed to a second distillation column K2 and separated therein into a water-rich overhead stream 7 and a bottom stream 8 comprising predominantly glycol. In the preferred process variant shown in the figure, a substream of the bottom stream 8 is discharged and the remainder of the bottom stream 8 is recycled to the reactive distillation column, into the ethylene glycol feed stream 1.

Figure 2:
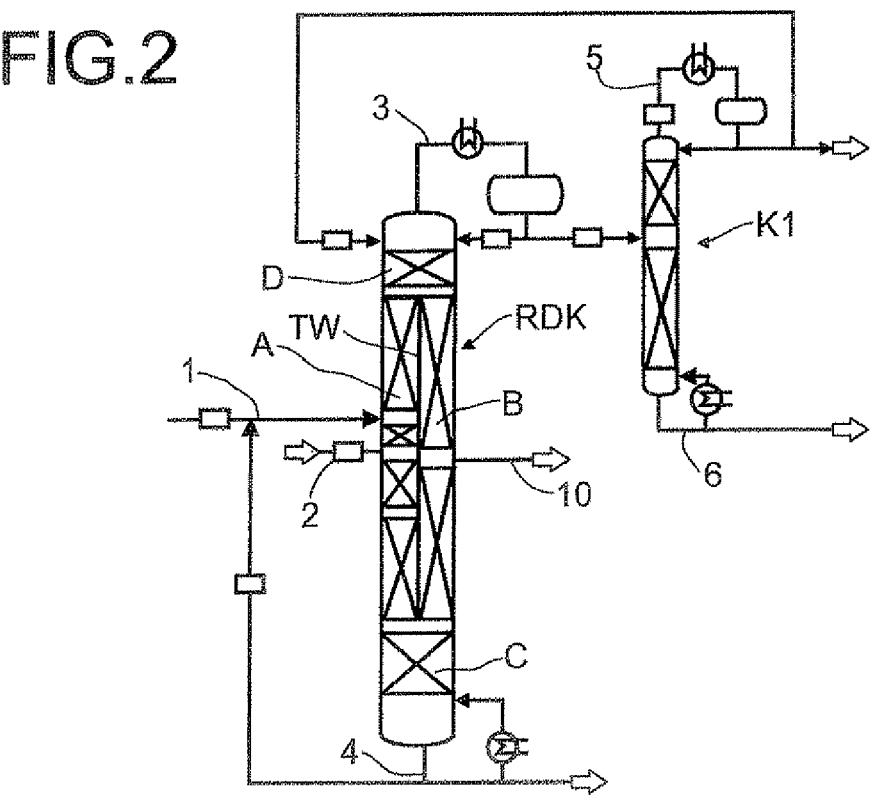

The process variant shown in FIG. 2 shows a reactive distillation column RDK which is configured as a dividing wall column and has a dividing wall TW which is aligned in the longitudinal direction of the column and divides the interior of the reactive distillation column RDK into a feed region A, an uptake region B, a lower combined column region C and an upper combined column region D.

The feed streams ethylene glycol (stream 1) and aqueous formaldehyde solution (stream 2) are introduced into the feed region; in the preferred process variant shown in the figure, stream 1 is introduced above stream 2. A water-rich stream 10 is taken off from the offtake section B and is fed to the wastewater requiring treatment. A stream 3 comprising the azeotrope of dioxolane/water is taken off from the upper combined column region D, condensed in a condenser at the top of the column, part of it is returned as runback to the reactive distillation column RDK and the remainder is fed to a first distillation column K1 which is operated at a pressure at the top which is higher than that in the reactive distillation column configured as dividing wall column and is separated therein into an overhead stream 5 comprising the azeotrope of dioxolane/water under the conditions of temperature and pressure at the top of the first distillation column K1, of which part is taken off and the remainder is recycled to the reactive distillation column RDK in the upper region thereof and a bottom stream 6 comprising pure dioxolane.

Figure 3:
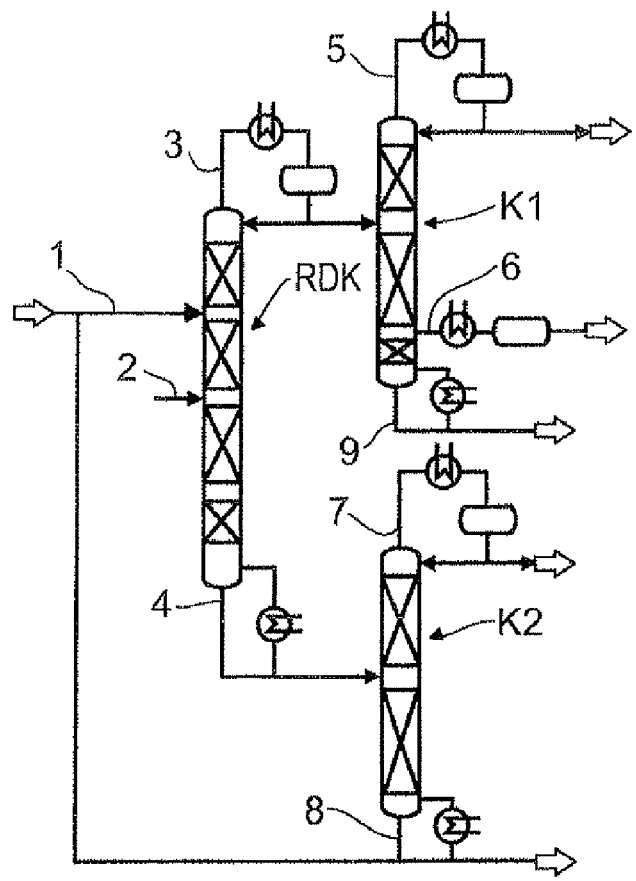

In the process variant shown in FIG. 3, the ethylene glycol feed stream 1 is fed in above the stream 2 of aqueous formaldehyde solution.

The overhead stream 3 from the reactive distillation column RDK is fed to a first distillation column K1 and separated therein into an overhead stream 5 comprising low boilers, the bottom stream 9 and a stream 6 from the lower region of the stripping section, which comprises pure dioxolane.

The bottom stream 4 from the reactive distillation column RDK is fed to a second distillation column K2 and separated therein into a water-rich overhead stream 7 and a bottom stream 8 comprising predominantly ethylene glycol, part of which is, in the preferred embodiment shown in FIG. 2, discharged and the remainder is recycled to the reactive distillation column RDK, into the ethylene glycol feed stream 1.

Figure 4:
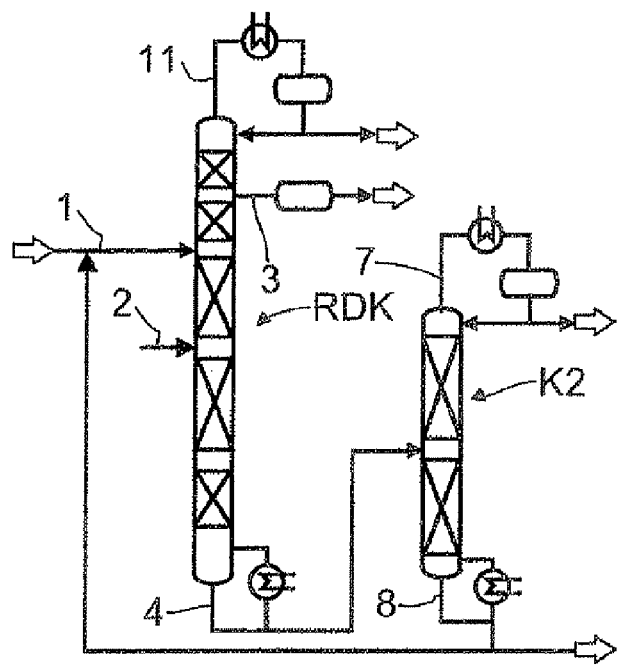

FIG. 4 shows a variant of the process depicted in FIG. 3 without the first distillation column K1; an overhead stream 11 comprising low boilers is taken off from the reactive distillation column RDK and, at a point below this, a pure dioxolane-comprising stream 3 is taken off from the upper region of the reactive distillation column RDK.

Figure 5:
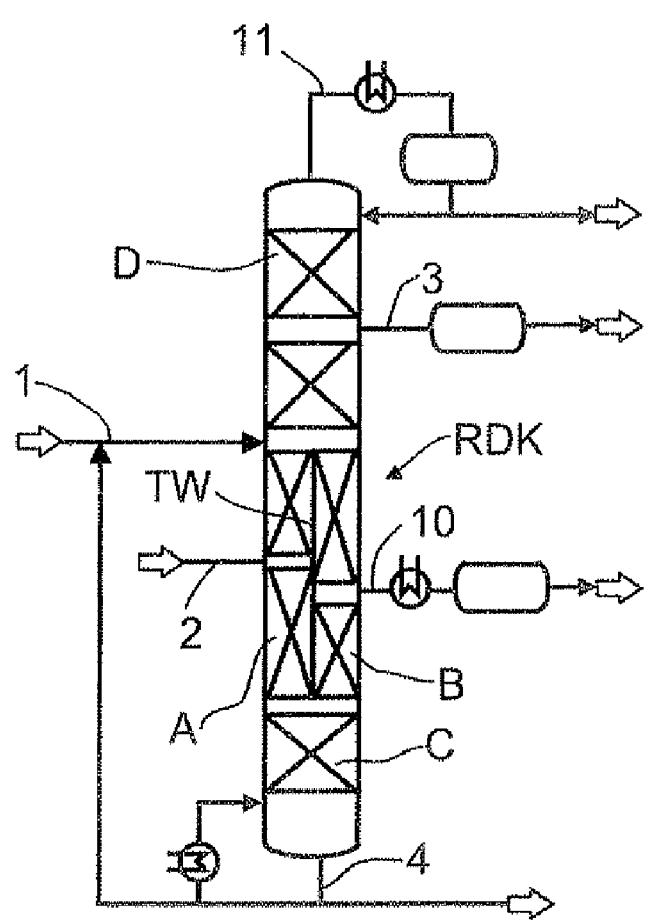

FIG. 5 shows a particularly preferred process variant having a single column, namely the reactive distillation column RDK which is configured as a dividing wall column having a dividing wall TW aligned in the longitudinal direction of the column. The ethylene glycol feed stream 1 is introduced in the upper part of the feed region A and the aqueous formaldehyde solution, stream 2, is introduced at a point below this in the middle part of the feed region A. A water-rich stream 10 is taken off from the offtake region, an overhead stream 11 comprising low boilers is taken off from the upper combined column region D and a stream 3 comprising pure dioxolane is taken off below this.

The bottom stream 4, which comprises predominantly ethylene glycol, is partly discharged and the remainder is recycled to the reactive distillation column configured as dividing wall column, into the ethylene glycol feed stream 1.

The invention claimed is:

1. A process comprising:
   providing a reactive distillation column having an upper region, a middle region and a lower region;
   feeding ethylene glycol and an aqueous formaldehyde solution into the reactive distillation column in the middle region of the reactive distillation column wherein ethylene glycol is fed into the reactive distillation column in a molar excess over formaldehyde in the aqueous formaldehyde solution and at an entry point above the aqueous formaldehyde solution such that the ethylene glycol is present in an amount greater than 25% by weight;
   reacting the ethylene glycol and the aqueous formaldehyde solution in the reactive distillation column in the presence of a catalyst to form dioxolane;
   removing a product stream comprising dioxolane in an amount of at least 95% by weight from the upper region of the reactive distillation column; and
   removing a bottom stream comprising one or more components having boiling points higher than dioxolane from the lower region of the reactive distillation column.

2. The process according to claim 1, wherein the reaction is carried out in the reactive distillation column at a top pressure of 0.01 to 50 bar absolute.

3. The process according to claim 1, wherein the reaction is carried out in the reactive distillation column at a top pressure of 0.15 to 2.5 bar absolute.

4. The process according to claim 1, wherein the reaction is carried out in the reactive distillation column at a top pressure of 0.2 to 1.5 bar absolute.

5. The process according to claim 1, wherein the product stream comprising dioxolane has the composition of an azeotrope of dioxolane and water under the conditions of temperature and pressure in the upper region of the reactive distillation column; further comprising feeding the product stream comprising dioxolane to a first distillation column operated at a top pressure greater than the top pressure of the reactive distillation column, removing an overhead stream from the first distillation column and recycling the overhead stream to the reactive distillation column, wherein the overhead stream has the composition of an azeotrope of dioxolane and water under the conditions of temperature and pressure at the top of the first distillation column; and removing a purified product stream comprising dioxolane in an amount greater than 95% by weight from a stripping section of the first distillation column.

6. The process according to claim 5, wherein the purified product stream removed from the stripping section of the first distillation column comprises dioxolane in an amount greater than 99% by weight.

7. The process according to claim 1, further comprising feeding the bottom stream to a second distillation column which is operated at a top pressure of 0.1 to 50 bar absolute, removing a water-rich overhead stream having a water content of greater than 75% by weight from the second distillation column; and removing a bottom stream which is rich in ethylene glycol from the second distillation column.

8. The process according to claim 7, wherein the second distillation column is operated at a top pressure of 0.15 to 2.5 bar absolute.

9. The process according to claim 7, wherein the water-rich overhead stream has a water content of greater than 99% by weight.

10. The process according to claim 7, further comprising separating the bottom stream from the second distillation column into a substream and a remainder stream, discharging the substream, and recycling the remainder stream to the reactive distillation column.

11. The process according to claim 1, wherein the reactive distillation column comprises a dividing wall column having a dividing wall disposed in a longitudinal direction of the column and which divides an interior of the reactive distillation column into a feed region, an offtake region, a lower combined column region and an upper combined column region, and wherein the ethylene glycol and aqueous formaldehyde solution are fed into the feed region, the product stream comprising dioxolane is removed from the upper combined column region and the bottom stream is removed from the lower combined column region, and wherein a water-rich stream having a water content of greater than 75% by weight is removed from the offtake region.

12. The process according to claim 11, wherein the water-rich stream has a water content of greater than 99% by weight.

13. The process according to claim 1, wherein the product stream comprises dioxolane in an amount of at least 99.5% by weight.

14. The process according to claim 1, further comprising removing an overhead stream comprising one or more components having boiling points lower than dioxolane from the reactive distillation column, feeding the bottom stream to a second distillation column which is operated at a top pressure of 0.1 to 50 bar absolute, and removing from the second distillation column a water-rich overhead stream having a water content of greater than 75% by weight and a bottom stream which is rich in ethylene glycol.

15. The process according to claim 1, further comprising removing an overhead stream comprising one or more components having boiling points lower than dioxolane from the reactive distillation column, feeding the bottom stream to a second distillation column which is operated at a top pressure of 0.15 to 2.5 bar absolute, and removing from the second distillation column a water-rich overhead stream having a water content of greater than 99% by weight and a bottom stream which is rich in ethylene glycol.

16. The process according to claim 1, wherein the reactive distillation column comprises a dividing wall column having a dividing wall disposed in a longitudinal direction of the column and which divides an interior of the reactive distillation column into a feed region, an offtake region, a lower combined column region and an upper combined column region, and wherein the ethylene glycol and aqueous formaldehyde solution are fed into the feed region, the product stream comprising dioxolane is removed from the upper combined column region and the bottom stream is removed from the lower combined column region, and wherein a water-rich stream having a water content of greater than 75% by weight is removed from the offtake region.

17. The process according to claim 1, wherein the product stream comprising dioxolane has the composition of an azeotrope of dioxolane and water under the conditions of temperature and pressure in the upper region of the reactive distillation column; further comprising feeding the product stream comprising dioxolane to a first distillation column having a top and a bottom and operated at a top pressure greater than the top pressure of the reactive distillation column, removing an overhead stream from the first distillation column and recycling the overhead stream to the reactive distillation column, wherein the overhead stream has the composition of an azeotrope of dioxolane and water under the conditions of temperature and pressure at the top of the first distillation column; and removing a purified product stream comprising dioxolane in an amount greater than 90% by weight from the bottom of the first distillation column.

* * * * *